United States Patent
Kropf et al.

(10) Patent No.: US 11,578,290 B2
(45) Date of Patent: Feb. 14, 2023

(54) ANIONIC SURFACTANTS AND DETERGENTS AND CLEANING AGENTS CONTAINING SAME

(71) Applicant: Henkel AG & Co. KGaA, Duesseldorf (DE)

(72) Inventors: Christian Kropf, Hilden (DE); Anna Klemmer, Duesseldorf (DE); Danuta Bedrunka, Dormagen (DE); Regina Palkovits, Aachen (DE); Peter Hausoul, Landgraaf (NL); Carsten Stobbe, Aachen (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 531 days.

(21) Appl. No.: 16/805,290

(22) Filed: Feb. 28, 2020

(65) Prior Publication Data

US 2020/0199489 A1   Jun. 25, 2020

Related U.S. Application Data

(63) Continuation of application No. PCT/EP2018/072407, filed on Aug. 20, 2018.

(30) Foreign Application Priority Data

Aug. 28, 2017 (DE) .......................... 102017008072.0

(51) Int. Cl.
| | | |
|---|---|---|
| *C11D 1/00* | (2006.01) | |
| *C11D 1/26* | (2006.01) | |
| *C07D 493/04* | (2006.01) | |
| *C11D 17/04* | (2006.01) | |
| *C11D 17/06* | (2006.01) | |

(52) U.S. Cl.
CPC .............. *C11D 1/26* (2013.01); *C07D 493/04* (2013.01); *C11D 17/042* (2013.01); *C11D 17/06* (2013.01)

(58) Field of Classification Search
CPC ................................ C11D 1/26; C07D 493/04
See application file for complete search history.

(56) References Cited

U.S. PATENT DOCUMENTS

| 4,448,779 | A | * | 5/1984 | Blanchard | .............. | A61K 31/44 |
|---|---|---|---|---|---|---|
| | | | | | | 514/301 |
| 5,643,562 | A | * | 7/1997 | Kisilevsky | ............. | A61K 31/70 |
| | | | | | | 526/287 |
| 8,173,797 | B2 | * | 5/2012 | Meinwald | .............. | C07H 19/10 |
| | | | | | | 536/17.6 |
| 2014/0275128 | A1 | * | 9/2014 | McVicar | ................ | A61K 31/52 |
| | | | | | | 514/263.23 |

FOREIGN PATENT DOCUMENTS

GB           952334 A        3/1964

OTHER PUBLICATIONS

Zhu, Yun-peng et al. "Preparation and Properties of Glycerol-Based Double-or Triple-Chain Surfactants With Two Hydrophilic Ionic Groups" Journal of The American Oil Chemists Society (JAOCS), vol. 69, No. 7, Jul. 1, 1992, pp. 626-632. DOI: 10.1007/BF02635800.
Fuentes, Jose et al."Completely Regioselective Synthesis of 5- and 6- Amino and Fluorohexofuranoses Via Cyclic Sulphates", Tetrahedron Letters, vol. 39, Elsevier Science Ltd., Sep. 24, 1998, pp. 7149-7152. DOI:10.1016/S0040-4039(98)01529-9.
Gourlain, Thierry et al. "Reaction of 5,6-Cyclic Sulfates Derived from Glycofuranoses with Bases. A One-Pot Synthesis of 6-Deoxy-Hexofuranos-5-Ulose Derivatives", Tetrahedron Letters, vol. 41, No. 5, Elsevier Science Ltd., Jan. 1, 2000, pp. 659-662. DOI: 10.1016/0040-4039(99)02158-9.
PCT International Search Report PCT/EP2018/072407 Completed: Oct. 18, 2018 dated Oct. 25, 2018 3 pages.

* cited by examiner

*Primary Examiner* — Necholus Ogden, Jr.
(74) *Attorney, Agent, or Firm* — Bojuan Deng

(57) ABSTRACT

The invention relates to surfactants of general formula (I) or general formula (II) or a mixture thereof, in which R represents a linear or branched alkyl, alkenyl, alkylaryl or alkenylaryl group having 5-25 C atoms and $X^+$ represents a charge-balancing cation. The surfactants can be incorporated into detergents or cleaning agents, have excellent technological application properties and can be produced based on renewable raw materials.

14 Claims, No Drawings

ANIONIC SURFACTANTS AND DETERGENTS AND CLEANING AGENTS CONTAINING SAME

FIELD OF THE INVENTION

The invention relates to anionic surfactants which can be prepared on the basis of renewable raw materials and which have low critical micelle concentrations (CMC) and produce low interfacial tensions. The invention also relates to a method for preparing such surfactants as well as to washing or cleaning agents which contain these surfactants.

BACKGROUND OF THE INVENTION

The use of surfactants to reduce the surface tension of water, to form dispersions, and for solubilization has been generally known in the field of washing and cleaning agents for a long time. Although many surfactants are produced completely or in part on the basis of renewable raw materials, some high-performing and widely-used representatives are still based on petrochemicals. In addition, there is a constant desire to provide surfactants having outstanding practical properties in order to be able to achieve high performance even with low surfactant use.

BRIEF SUMMARY OF THE INVENTION

The object of the present invention is to provide surfactants which have advantageous practical properties, such as a low CMC and a low surface tension, and can be prepared on the basis of renewable raw materials. In addition, the surfactants are intended to have good skin compatibility and it should also be possible to prepare them together with other surfactants so that they are particularly suitable for use in washing and cleaning agents.

In a first embodiment, the present invention relates to an anionic surfactant of general formula (I) or of general formula (II) or a mixture thereof,

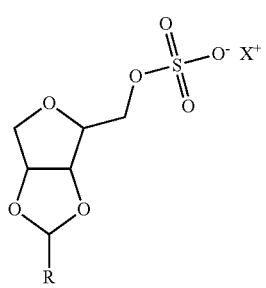
(I)

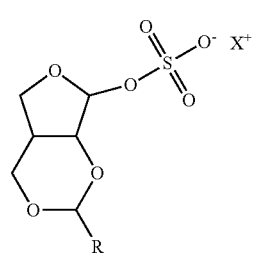
(II)

in which R is a linear or branched alkyl, alkenyl, alkylaryl or alkenylaryl group having 5 to 25 C atoms and $X^+$ is a charge-balancing cation. $X^+$ is preferably selected from the group comprising the proton, alkali metal cations and the grouping $N^+R^1R^2R^3$, in which $R^1$, $R^2$ and $R^3$ are, independently of one another, hydrogen, an alkyl group having 1 to 6 C atoms or a hydroxyalkyl group having 2 to 6 C atoms.

Preferred surfactants of general formula (I) are those in which R is a linear or branched alkyl group having 7 C atoms to 21 C atoms, with linear groups R, including those having an odd number of C atoms, being particularly preferred.

Surfactants of general formulas (I) and (II) and mixtures thereof can be prepared by sulfation of compounds of general formulas (III), (IV) and mixtures thereof

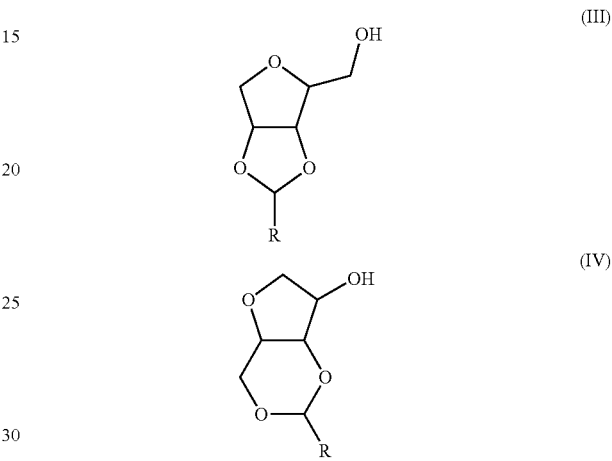

in which R has the meaning specified above, using a sulfating agent, for example chlorosulfonic acid or sulfur trioxide pyridine, and optionally neutralization by subsequent reaction with $X^+OH^-$, $X^+HCO^-_3$ or $X^+_2CO^{2-}_3$, where $X^+$ has the meaning specified above. Compounds of general formulas (III) and (IV), in particular mixtures thereof, can be obtained by acetalization of 2-hydroxymethyl-tetrahydrofuran-3,4-diol, in particular by the acid-catalyzed reaction thereof with aldehydes. The compounds of general formula (III) can be separated from those of general formula (IV) by conventional methods of organic chemistry. The same applies to the compounds of general formulas (I) and (II) when mixtures thereof have been produced from mixtures of compounds of general formulas (III) and (IV). 2-Hydroxymethyl-tetrahydrofuran-3,4-diol can be prepared by acid-induced cyclization of pentitols. Depending on whether ribitol, D- or L-arabitol, or xylitol is the starting point, and which terminal C atom of the pentitol forms part of the tetrahydrofuran ring, different configurations can result at the three chiral centers of the trisubstituted tetrahydrofuran ring; reaction with the aldehyde results in another chiral center on the original carbonyl C atom thereof. The compounds of general formulas (I), (II), (III) and (IV) are therefore usually present as stereoisomer mixtures, depending on production. Pentitols can be obtained by the reduction of pentoses; they can also be obtained by the reductive cleavage of hemicellulose, with in particular ribitol being produced. Pentoses and hemicelluloses can be obtained from a variety of plants.

The invention also relates to a method for preparing above-defined compounds of general formulas (I) or (II) or mixtures thereof by a) acid-induced separation of water from ribitol, arabitol, xylitol or mixtures thereof, b) reaction of the 2-hydroxymethyl-tetrahydrofuran-3,4-diol obtained in this way with an aldehyde RCHO, in which R has the meaning specified above, in particular selected from heptaldehyde, caprylaldehyde, pelargonaldehyde, lauric aldehyde, myristic aldehyde, palmitaldehyde, stearaldehyde, oleylaldehyde, elaidylaldehyde, linoleylaldehyde, linolenylaldehyde and mixtures thereof, and c) subsequent sulfation using a sulfating agent and optionally neutralization by subsequent reaction with $X^+OH^-$, $X^+HCO^-_3$ or $X^+_2CO^{2-}_3$, where $X^+$ is an alkali metal cation or a grouping $N^+R^1R^2R^3$, in which $R^1$, $R^2$ and $R^3$ are, independently of one another, hydrogen, an alkyl group having 1 to 6 C atoms or a hydroxyalkyl group having 2 to 6 C atoms.

The surfactants according to the invention have very low CMC values and result in very low interfacial tensions with respect to oil with rapid dynamics in terms of organization at the interface. Particularly preferred surfactants according to the invention have a CMC of from 0.005 g/l to 0.2 g/l in water at pH 8.5 and 25° C. and produce an interfacial tension, which can be determined with respect to isopropyl myristate by means of the spinning drop method (20-minute equilibration time) at a concentration of 1 g/l in water at pH 8.5 and 25° C., of less than 8 mN/m, in particular in the range of from 1 mN/m to 5 mN/m.

The surfactants according to the invention can be obtained, as described, from renewable raw materials. They also have the advantage that the renewable raw materials from which they can be produced include those which do not provide a basis for the production of food, so that the food competition situation observed with some surfactants that can be obtained from other renewable raw materials is not present here.

The surfactants according to the invention are preferably prepared by reacting a pentitol, in particular ribitol or a ribitol-containing pentitol mixture, by exposure to acid, for example an aqueous sulfuric acid solution, at a temperature in the range of from 100° C. to 110° C. and a duration in the range of preferably from 16 hours to 24 hours, to form 3,4-dihydroxy-2-hydroxymethyl-tetrahydrofuran. This is preferably reacted in acid catalysis with an aldehyde having 7 to 25 C atoms, with this preferably being carried out at temperatures in the range of from 60° C. to 90° C. and a duration in the range of from 24 hours to 72 hours.

A compound obtained in this way is reacted with a sulfating agent, for example chlorosulfonic acid or sulfur trioxide pyridine, at a temperature in the range of from preferably −20° C. to 75° C., in particular from 25° C. to 75° C., and for a duration in the range of preferably from 1 hour to 24 hours, in particular 6 to 18 hours. Subsequently, the charge-balancing cation present after sulfation can be replaced, if desired, by reaction with $X^+OH^-$, for example 1 M methanolic sodium hydroxide solution, or by reaction with $X^+HCO^-_3$ or $X^+_2CO^{2-}_3$, for example sodium hydrogen carbonate or sodium carbonate. The isolation of the surfactant of general formula (I) can take place for example by precipitation when a suitable precipitant is added, in particular acetone or petroleum ether.

The surfactants according to the invention are highly suitable as an ingredient in washing and cleaning agents, cosmetics such as shampoos and toothpastes, and for other applications in which anionic surfactants are currently conventionally used, such as in the food industry, geosciences, tertiary oil production, plastics technology, metalworking, photography, paper recycling, tool cleaning, and fire-fighting.

DETAILED DESCRIPTION OF THE INVENTION

Particularly good results are achieved in the use thereof in washing and cleaning agents, and therefore the present invention also relates to the use of anionic surfactant of general formula (I) for the preparation of washing or cleaning agents, to the use of an anionic surfactant of general formula (I) or of general formula (II) or a mixture thereof for enhancing the performance of washing or cleaning agents when washing laundry or cleaning hard surfaces, and to the washing or cleaning agents containing a surfactant of general formula (I) or of general formula (II) or a mixture thereof.

A washing or cleaning agent according to the invention preferably contains 1 wt. % to 99 wt. %, in particular 3 wt. % to 65 wt. %, and particularly preferably 5 wt. % to 45 wt. %, of the surfactant of general formula (I) or of general formula (II) or a mixture thereof.

In addition to the anionic surfactant of general formula (I) or of general formula (II) or the mixture thereof, the washing or cleaning agent may contain further ingredients which further improve the practical and/or esthetic properties of the agent. In the context of the present invention, the agent preferably additionally contains one or more substances from the group of non-ionic surfactants, anionic surfactants, builders, bleaching agents, bleach activators, enzymes, electrolytes, pH adjusters, perfumes, perfume carriers, fluorescing agents, dyes, hydrotropes, suds suppressors, anti-redeposition agents, graying inhibitors, anti-shrink agents, anti-crease agents, dye transfer inhibitors, antimicrobial active ingredients, non-aqueous solvents, germicides, fungicides, antioxidants, preservatives, corrosion inhibitors, antistatic agents, bittering agents, ironing aids, repellents and impregnating agents, skin care active ingredients, anti-swelling and anti-slip agents, softening components and UV absorbers.

A washing or cleaning agent according to the invention preferably contains, in addition to the anionic surfactant of the surfactant of general formula (I) or of general formula (II) or a mixture thereof, up to 99 wt. %, in particular 3 wt. % to 65 wt. %, and particularly preferably 5 wt. % to 45 wt. %, of additional surfactant, the additionally present surfactants preferably also being obtainable from renewable raw materials.

The agent according to the invention may contain non-ionic surfactants. Suitable non-ionic surfactants include alkoxylated fatty alcohols, alkoxylated fatty acid alkyl esters, fatty acid amides, alkoxylated fatty acid amides, polyhydroxy fatty acid amides, alkylphenol polyglycol ethers, amine oxides, alkyl polyglucosides, and mixtures thereof.

Alkoxylated fatty alcohols that are preferably used are ethoxylated, in particular primary alcohols having preferably 8 to 18 C atoms and, on average, 4 to 12 mol ethylene oxide (EO) per mol of alcohol, in which the alcohol functional group is linear. In particular, alcohol ethoxylates having 12 to 18 C atoms, for example from coconut, palm, tallow fatty or oleyl alcohol, and, on average, 5 to 8 EO per mol of alcohol are particularly preferred. Preferred ethoxylated alcohols include, for example, $C_{12-14}$ alcohols having 4 EO or 7 EO, $C_{9-11}$ alcohols having 7 EO, $C_{12-18}$ alcohols having 5 EO or 7 EO, and mixtures thereof. The degrees of ethoxylation specified represent statistical averages that can correspond to an integer or a fractional number for a specific product. Preferred alcohol ethoxylates have a narrowed homolog distribution (narrow range ethoxylates, NRE). In addition to these non-ionic surfactants, fatty alcohols having more than 12 EO can also be used. Examples of these are tallow fatty alcohols having 14 EO, 25 EO, 30 EO, or 40 EO. Non-ionic surfactants that contain EO and PO groups together in the molecule can also be used according to the invention. Furthermore, a mixture of a (more highly)

branched ethoxylated fatty alcohol and an unbranched ethoxylated fatty alcohol, such as a mixture of a $C_{16-18}$ fatty alcohol having 7 EO and 2-propylheptanol having 7 EO, is also suitable. The amount of non-ionic surfactant is preferably up to 25 wt. %, in particular 1 wt. % to 20 wt. %, the weight percentages here and in the following being based in each case on the total washing agent, if not stated otherwise.

Optionally additionally present anionic surfactants include alkylbenzene sulfonic acid salts, olefin sulfonic acid salts, $C_{12-18}$ alkanesulfonic acid salts, salts of sulfuric acid monoesters with a fatty alcohol, fatty acid soaps, salts of sulfuric acid monoesters with an ethoxylated fatty alcohol, or a mixture of two or more of these anionic surfactants.

Surfactants of the sulfonate type that can be used are for example $C_{9-13}$ alkylbenzene sulfonates, olefin sulfonates, i.e. mixtures of alkene and hydroxyalkane sulfonates, and disulfonates, as obtained, for example, from $C_{12-18}$ monoolefins having a terminal or internal double bond by way of sulfonation with gaseous sulfur trioxide and subsequent alkaline or acid hydrolysis of the sulfonation products. $C_{12-18}$ alkane sulfonates and the esters of α-sulfofatty acids (ester sulfonates), for example the α-sulfonated methyl esters of hydrogenated coconut, palm kernel or tallow fatty acids, are also suitable.

The salts of the sulfuric acid half-esters of $C_{12}$-$C_{18}$ fatty alcohols, for example from coconut fatty alcohol, tallow fatty alcohol, lauryl, myristyl, cetyl or stearyl alcohol, or of $C_{10}$-$C_{20}$ oxo alcohols and the half-esters of secondary alcohols having these chain lengths are preferred as alk(en)yl sulfates. From a washing perspective, $C_{12}$-$C_{16}$ alkyl sulfates, $C_{12}$-$C_{15}$ alkyl sulfates and $C_{14}$-$C_{15}$ alkyl sulfates are preferred.

Fatty alcohol ether sulfates, such as the sulfuric acid monoesters of straight-chain or branched $C_{7-21}$ alcohols ethoxylated with 1 to 6 mol of ethylene oxide, such as 2-methyl-branched $C_{9-11}$ alcohols having, on average, 3.5 mol of ethylene oxide (EO) or $C_{12-18}$ fatty alcohols having 1 to 4 EO, are also suitable.

Other suitable anionic surfactants are fatty acid soaps. Saturated and unsaturated fatty acid soaps are suitable, such as the salts of lauric acid, myristic acid, palmitic acid, stearic acid, (hydrogenated) erucic acid and behenic acid, and in particular soap mixtures derived from natural fatty acids, such as coconut, palm kernel, olive oil or tallow fatty acids.

The additional anionic surfactants including the fatty acid soaps can be present in the form of the sodium, potassium or magnesium or ammonium salts thereof. The anionic surfactants are preferably present in the form of the sodium salts or ammonium salts thereof. Amines that can be used for neutralization are preferably choline, triethylamine, monoethanolamine, diethanolamine, triethanolamine, methylethylamine, or a mixture thereof, with monoethanolamine being preferred. In a particularly preferred embodiment, the agent contains, in particular when in liquid form, monoethanolamine-neutralized alkylbenzenesulfonic acid, in particular $C_{9-13}$ alkylbenzenesulfonic acid, and/or monoethanolamine-neutralized fatty acid.

The content of additional anionic surfactant, if any, in the agent according to the invention is preferably up to 30 wt. %, in particular 1 wt. % to 25 wt. %.

An agent according to the invention preferably contains at least one water-soluble and/or water-insoluble, organic and/or inorganic builder. The water-soluble organic builder substances include polycarboxylic acids, in particular citric acid and saccharic acids, monomeric and polymeric aminopolycarboxylic acids, in particular glycinediacetic acid, methylglycinediacetic acid, nitrilotriacetic acid, iminodisuccinates such as ethylenediamine-N,N'-disuccinic acid and hydroxyiminodisuccinate, ethylenediaminetetraacetic acid and polyaspartic acid, polyphosphonic acids, in particular aminotris(methylenephosphonic acid), ethylenediamine tetrakis (methylenephosphonic acid), lysine tetra(methylenephosphonic acid) and 1-hydroxyethane-1,1-diphosphonic acid, polymeric hydroxy compounds such as dextrin, and polymeric (poly)carboxylic acids, in particular polycarboxylates which can be obtained by oxidizing polysaccharides, polymeric acrylic acids, methacrylic acids, maleic acids, and mixed polymers thereof, which may also contain, in the polymer, small proportions of polymerizable substances without a carboxylic acid functionality. The relative average molecular mass of the homopolymers of unsaturated carboxylic acids is generally between 5,000 g/mol and 200,000 g/mol, and that of the copolymers is between 2,000 g/mol and 200,000 g/mol, preferably 50,000 g/mol to 120,000 g/mol, in each case based on free acid. A particularly preferred acrylic acid-maleic acid copolymer has a relative average molecular mass of from 50,000 to 100,000. Compounds of this class which are suitable, although less preferred, are copolymers of acrylic acid or methacrylic acid with vinyl ethers, such as vinyl methyl ethers, vinyl esters, ethylene, propylene and styrene, in which the proportion of the acid is at least 50 wt. %. It is also possible to use, as water-soluble organic builder substances, terpolymers which contain two unsaturated acids and/or the salts thereof as monomers and vinyl alcohol and/or a vinyl alcohol derivative or a carbohydrate as a third monomer. The first acid monomer or the salt thereof is derived from a monoethylenically unsaturated $C_3$-$C_8$ carboxylic acid and preferably from a $C_3$-$C_4$ monocarboxylic acid, in particular from (meth)acrylic acid. The second acid monomer or the salt thereof can be a derivative of a $C_4$-$C_8$ dicarboxylic acid, with maleic acid being particularly preferred. The third monomeric unit is formed in this case of vinyl alcohol and/or preferably an esterified vinyl alcohol. In particular, vinyl alcohol derivatives are preferred which are an ester of short-chain carboxylic acids, for example $C_1$-$C_4$ carboxylic acids, with vinyl alcohol. Preferred polymers contain 60 wt. % to 95 wt. %, in particular 70 wt. % to 90 wt. %, (meth)acrylic acid or (meth)acrylate, particularly preferably acrylic acid or acrylate, and maleic acid or maleate, and 5 wt. % to 40 wt. %, preferably 10 wt. % to 30 wt. %, of vinyl alcohol and/or vinyl acetate. Very particularly preferred are polymers in which the weight ratio of (meth)acrylic acid or (meth)acrylate to maleic acid or maleate is between 1:1 and 4:1, preferably between 2:1 and 3:1, and in particular between 2:1 and 2.5:1. Both the amounts and the weight ratios are based on the acids. The second acid monomer or the salt thereof can also be a derivative of an allylsulfonic acid which is substituted in the 2 position with an alkyl functional group, preferably with a $C_1$-$C_4$ alkyl functional group, or an aromatic functional group which is preferably derived from benzene or benzene derivatives. Preferred terpolymers contain 40 wt. % to 60 wt. %, in particular 45 to 55 wt. %, (meth)acrylic acid or (meth)acrylate, particularly preferably acrylic acid or acrylate, 10 wt. % to 30 wt. %, preferably 15 wt. % to 25 wt. %, methallylsulfonic acid or methallylsulfonate and 15 wt. % to 40 wt. %, preferably 20 wt. % to 40 wt. %, carbohydrate as a third monomer. This carbohydrate may be, for example, a mono-, di-, oligo- or polysaccharide, with mono-, di- or oligosaccharides being preferred. Sucrose is particularly preferred. The use of the third monomer presumably incorporates predetermined breaking points into the polymer which are responsible for the good biodegradability of the polymer. These terpolymers generally have a relative average molecular mass between 1,000 g/mol and 200,000 g/mol, preferably between 200 g/mol and 50,000 g/mol. Further preferred copolymers are those which have acrolein and acrylic acid/acrylic acid salts or vinyl acetate as monomers. The organic builder substances may, in particular for the preparation of liquid agents, be used in the form of aqueous solutions, preferably in the form of 30 to 50 wt. % aqueous solutions. All mentioned acids are generally used in the form of the water-soluble salts thereof, in particular the alkali salts thereof.

Organic builder substances of this kind can, if desired, be contained in amounts of up to 40 wt. %, in particular up to 25 wt. %, and preferably from 1 wt. % to 8 wt. %. Amounts in the upper half of the stated ranges are preferably used in paste-like or liquid, in particular water-containing, agents.

In particular polyphosphates, preferably sodium triphosphate, are suitable as water-soluble inorganic builder materials. In particular crystalline or amorphous, water-dispersible alkali aluminosilicates are used as water-insoluble inorganic builder materials in amounts not exceeding 25 wt. %, preferably from 3 wt. % to 20 wt. %, and in particular in amounts of from 5 wt. % to 15 wt. %. Of these, the crystalline sodium aluminosilicates of washing agent quality, in particular zeolite A, zeolite P, and zeolite MAP, and optionally zeolite X, are preferred. Amounts close to the stated upper limit are preferably used in solid particulate agents. Suitable aluminosilicates have in particular no particles having a particle size greater than 30 μm and preferably consist up to at least 80 wt. % of particles having a size smaller than 10 μm. The calcium binding capacity of said aluminosilicates is generally in the range of from 100 to 200 mg CaO per gram.

In addition or as an alternative to said water-insoluble aluminosilicate and alkali carbonate, further water-soluble inorganic builder materials may be contained. These include, in addition to the polyphosphates such as sodium triphosphate, in particular the water-soluble crystalline and/or amorphous alkali silicate builders. Water-soluble inorganic builder materials of this kind are contained in the agents preferably in amounts of from 1 wt. % to 20 wt. %, in particular from 5 wt. % to 15 wt. %. The alkali silicates that can be used as builder materials preferably have a molar ratio of alkali oxide to $SiO_2$ of less than 0.95, in particular from 1:1.1 to 1:12, and may be present in amorphous or crystalline form. Preferred alkali silicates are sodium silicates, in particular amorphous sodium silicates, having a $Na_2O$: $SiO_2$ molar ratio of from 1:2 to 1:2.8. Crystalline phyllosilicates of general formula $Na_2Si_xO_{2x+1} \cdot y\ H_2O$, where x, referred to as the module, is a number from 1.9 to 4, y is a number from 0 to 20, and preferred values for x are 2, 3 or 4, are preferably used as crystalline silicates, which may be present alone or in a mixture with amorphous silicates. Preferred crystalline phyllosilicates are those in which x in the stated general formula assumes the values 2 or 3. In particular, both ß- and δ-sodium disilicates ($Na_2Si_2O_5 \cdot y\ H_2O$) are preferred. Practically water-free crystalline alkali silicates of the above general formula, where x is a number from 1.9 to 2.1, which are prepared from amorphous alkali silicates may also be used in the agents. In a further preferred embodiment, a crystalline sodium phyllosilicate having a module of from 2 to 3, as can be produced from sand and soda, is used. Sodium silicates having a module in the range of from 1.9 to 3.5 are used in a further embodiment. In a preferred embodiment of such agents, a granular compound of alkali silicate and alkali carbonate is used, as is commercially available, for example, under the name Nabion® 15.

Suitable peroxidic bleaching agents may be in particular organic peracids or peracid salts of organic acids, such as phthalimidopercaproic acid, perbenzoic acid, monoperoxyphthalic acid, and diperdodecane diacid and salts thereof, such as magnesium monoperoxyphthalate, diacyl peroxides, hydrogen peroxide and inorganic salts which release hydrogen peroxide under the conditions of use, such as alkali perborate, alkali percarbonate and/or alkali persilicate, and hydrogen peroxide inclusion compounds, such as $H_2O_2$ urea adducts, and mixtures thereof. Hydrogen peroxide can also be produced by means of an enzymatic system, i.e. an oxidase and the substrate thereof. If solid peroxygen compounds are intended to be used, these may be used in the form of powders or granules, which may also be coated in a manner known in principle. Particularly preferably, alkali percarbonate, alkali perborate monohydrate or hydrogen peroxide is used. A washing agent which can be used in the context of the invention comprises peroxidic bleaching agent in amounts of preferably up to 60 wt. %, in particular from 5 wt. % to 50 wt. %, and particularly preferably from 15 wt. % to 30 wt. % or, alternatively, from 2.5 wt. % to 20 wt. %, hydrogen peroxide being the most preferred peroxidic bleaching agent in liquid agents and sodium percarbonate being most preferred in solid agents. Peroxidic bleaching agent particles preferably have a particle size in the range of from 10 μm to 5,000 μm, in particular from 50 μm to 1,000 μm, and/or a density from 0.85 g/cm³ to 4.9 g/cm³, in particular from 0.91 g/cm³ to 2.7 g/cm³.

In particular compounds which produce, under perhydrolysis conditions, optionally substituted perbenzoic acid and/or aliphatic peroxycarboxylic acids having 1 to 12 C atoms, in particular 2 to 4 C atoms, alone or in mixtures, are used as a bleach-activating compound that produces peroxycarboxylic acid under perhydrolysis conditions. Bleach activators that have O- and/or N-acyl groups in particular of the stated number of C atoms and/or optionally substituted benzoyl groups are suitable. Preferred are polyacylated alkylenediamines, in particular tetraacetylethylenediamine (TAED), acylated glycolurils, in particular tetraacetylglycoluril (TAGU), acylated triazine derivatives, in particular 1,5-diacetyl-2,4-dioxohexahydro-1,3,5-triazine (DADHT), N-acylimides, in particular N-nonanoylsuccinimide (NOSI), acylated phenolsulfonates or carboxylates or the sulfonic or carboxylic acids thereof, in particular nonanoyl or isononanoyl or lauroyl oxybenzenesulfonate (NOBS or iso-NOBS or LOBS) or decanoyloxybenzoate (DOBA), the formal carbonic acid ester derivatives thereof such as 4-(2-decanoyloxyethoxycarbonyloxy)-benzenesulfonate (DECOBS), acylated polyhydric alcohols, in particular triacetin, ethylene glycol diacetate and 2,5-di-acetoxy-2,5-dihydrofuran and acetylated sorbitol and mannitol and mixtures thereof (SORMAN), acylated sugar derivatives, in particular pentaacetylglucose (PAG), pentaacetylfructose, tetraacetylxylose and octaacetyl lactose, acetylated, optionally N-alkylated glucamine and gluconolactone, and/or N-acylated lactams, for example N-benzoyl-caprolactam.

In addition to, or instead of, the compounds which form peroxycarboxylic acids under perhydrolysis conditions, other bleach-activating compounds, such as nitriles, from which perimidic acids may form under perhydrolysis conditions, may be present. These include in particular aminoacetonitrile derivatives having a quaternized nitrogen atom according to the formula

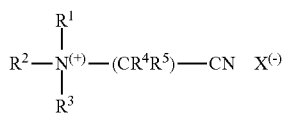

in which: $R^1$ is —H, —$CH_3$, a $C_{2-24}$ alkyl or $C_{2-24}$ alkenyl functional group, a substituted $C_{1-24}$ alkyl or $C_{2-24}$ alkenyl functional group having at least one substituent from the group —Cl, —Br, —OH, —$NH_2$, —CN and —$N^{(+)}$—$CH_2$—CN, an alkyl or alkenylaryl functional group having a $C_{1-24}$ alkyl group, or a substituted alkyl- or alkenylaryl functional group having at least one, preferably two, optionally substituted $C_{1-24}$ alkyl group(s) and optionally further substituents on the aromatic ring; $R^2$ and $R^3$ are selected, independently of one another, from —$CH_2$—CN, —$CH_3$, —$CH_2$—$CH_3$, $CH_2$—$CH_2$—$CH_3$, —$CH(CH_3)$—$CH_3$, —$CH_2$—OH, —$CH_2$—$CH_2$—OH, —$CH(OH)$—$CH_3$, —$CH_2$—$CH_2$—$CH_2$—OH, —$CH_2$—$CH(OH)$—$CH_3$, —$CH(OH)$—$CH_2$—$CH_3$, —$(CH_2CH_2$—$O)_n$H where n=1, 2, 3, 4, 5 or 6; $R^4$ and $R^5$ have, independently of one another, the meaning specified above for $R^1$, $R^2$ or $R^3$, where at least two of the functional groups mentioned, in particular $R^2$ and $R^3$, also including the nitrogen atom and possibly other heteroatoms, can be linked to one another in a ring-closing manner and then preferably form a morpholino ring; and X is a charge-balancing anion, preferably selected from benzenesulfonate, toluenesulfonate, cumenesulfonate, the $C_{9-15}$ alkylbenzenesulfonates, the $C_{1-20}$ alkyl sulfates, the $C_{8-22}$ carboxylic acid methyl ester sulfonates, sulfate, hydrogen sulfate, and mixtures thereof, may be used. Bleach activators forming peroxycarboxylic acids or perimidic acids under perhydrolysis conditions are preferably present in agents according to the invention in amounts of up to 25 wt. %, in particular 0.1 wt. % to 10 wt. %. Bleach activator particles preferably have a particle size in the range of from 10 μm to 5,000 μm, in particular from 50 μm to 1,000 and/or a density from 0.85 g/cm³ to 4.9 g/cm³, in particular from 0.91 g/cm³ to 2.7 g/cm³.

The presence of bleach-catalyzing transition metal complexes, in addition to or instead of said bleach activators, is possible. These are preferably selected from the cobalt, iron, copper, titanium, vanadium, manganese and ruthenium complexes. Suitable ligands in such transition metal complexes are both inorganic and organic compounds, which include, in addition to carboxylates, in particular compounds having primary, secondary and/or tertiary amine and/or alcohol functions, such as pyridine, pyridazine, pyrimidine, pyrazine, imidazole, pyrazole, triazole, 2,2'-bispyridylamine, tris-(2-pyridylmethyl)amine, 1,4,7-triazacyclononane, 1,4, 7-trimethyl-1,4,7-triazacyclononane, 1,5,9-trimethyl-1,5,9-triazacyclododecane, (bis-((1-methylimidazol-2-yl)-methyl))-(2-pyridylmethyl)-amine, N,N'-(bis-(1-methylimidazol-2-yl)-methyl)-ethylenediamine, N-bis-(2-benzimidazolylmethyl)-aminoethanol, 2,6-bis-(bis-(2-benzimidazolylmethyl)aminomethyl)-4-methylphenol, N,N, N',N'-tetrakis-(2-benzimidazolylmethyl)-2-hydroxy-1,3-diaminopropane, 2,6-bis-(bis-(2-pyridylmethyl) aminomethyl)-4-methylphenol, 1,3-bis-(bis-(2-benzimidazolylmethyl)aminomethyl)-benzene, sorbitol, mannitol, erythritol, adonitol, inositol, lactose, and optionally substituted salenes, porphins and porphyrins. The inorganic neutral ligands include in particular ammonia and water. If not all coordination sites of the transition metal central atom are occupied by neutral ligands, the complex contains further, preferably anionic ligands, of these in particular mono- or bidentate ligands. These include in particular the halides such as fluoride, chloride, bromide and iodide, and the ($NO_2$) group, i.e. a nitro ligand or a nitrito ligand. The ($NO_2$) group may also be chelated to a transition metal or it may asymmetrically or μl-O-bridge two transition metal atoms. In addition to the ligands mentioned, the transition metal complexes may carry further, generally more simple ligands, in particular mono- or polyvalent anion ligands. For example, nitrate, acetate, trifluoroacetate, formate, carbonate, citrate, oxalate, perchlorate, and complex anions such as hexafluorophosphate are suitable. The anion ligands are intended to ensure charge balance between the transition metal central atom and the ligand system. The presence of oxo ligands, peroxo ligands and imino ligands is also possible. In particular, such ligands can also have a bridging effect, such that polynuclear complexes are produced. In the case of bridged, binuclear complexes, the two metal atoms in the complex do not need to be the same. The use of binuclear complexes in which the two transition metal central atoms have different oxidation numbers is also possible. If anion ligands are missing or the presence of anionic ligands does not result in charge balance in the complex, anionic counterions which neutralize the cationic transition metal complex are present in the transition metal complex compounds to be used according to the invention. These anionic counterions include in particular nitrate, hydroxide, hexafluorophosphate, sulfate, chlorate, perchlorate, the halides such as chloride or the anions of carboxylic acids such as formate, acetate, oxalate, benzoate or citrate. Examples of transition metal complex compounds that can be used are [N,N'-bis[(2-hydroxy-5-vinylphenyl)methylene]-1,2-diamino-cyclohexane] manganese(III) chloride, [N,N'-bis[(2-hydroxy-5-nitrophenyl)methylene]-1,2-diamino-cyclohexane] manganese(III) acetate, [N,N'-bis[(2-hydroxyphenyl)methylene]-1,2-phenylenediamine] manganese(III) acetate, [N,N' -bis[(2-hydroxyphenyl)methylene]-1,2-diaminocyclohexane] manganese(III) chloride, [N,N'-bis[(2-hydroxyphenyl)methylene]-1,2-diaminoethane] manganese(III) chloride, [N,N'-bis[(2-hydroxy-5-sulfonato-phenyl)methylene]-1,2-diaminoethane] manganese(III) chloride, manganese oxalate complexes, nitropentamine cobalt(III) chloride, nitritopentaamminecobalt(III) chloride, hexamminecobalt(III) chloride, chloropentamminecobalt (III) chloride and the peroxo complex [($NH_3)_5$Co—O—CO ($NH_3)_5]Cl_4$.

Enzymes from the class of proteases, amylases, lipases, cutinases, pullulanases, hemicellulases, cellulases, oxidases, laccases and peroxidases, and mixtures thereof are suitable as enzymes that can be used in the agents. Enzymatic active ingredients obtained from fungi or bacteria, such as *Bacillus subtilis, Bacillus licheniformis, Bacillus lentus, Streptomyces griseus*, Humicola lanuginosa, Humicola insolens, *Pseudomonas pseudoalcaligenes, Pseudomonas cepacia*, or Coprinus cinereus are particularly suitable. The enzymes can be adsorbed on carrier substances and/or embedded in coating substances to protect the enzymes from premature inactivation. They are contained in the washing or cleaning agents according to the invention preferably in amounts of up to 5 wt. %, in particular from 0.002 wt. % to 4 wt. %. If the agent according to the invention contains protease, it preferably has a proteolytic activity in the range of from approximately 100 PE/g to approximately 10,000 PE/g, in particular 300 PE/g to 8,000 PE/g. If a plurality of enzymes are to be used in the agent according to the invention, this can be carried out by incorporation of the two or more separate or, in a known manner, separately prepared enzymes or by two or more enzymes prepared together in a granulate.

In order to set a desired pH that does not result automatically from mixing the other components, the agents according to the invention can contain acids that are compatible with the system and the environment, in particular citric acid, acetic acid, tartaric acid, malic acid, lactic acid, glycolic acid, succinic acid, glutaric acid, and/or adipic acid, but also mineral acids, in particular sulfuric acid, or bases, in particular ammonium or alkali hydroxides. Such pH regulators are contained in the agents according to the invention in amounts of preferably no greater than 20 wt. %, in particular from 1.2 wt. % to 17 wt. %.

The function of graying inhibitors is to keep the dirt that is removed from the textile fiber suspended in the liquor. Water-soluble colloids, which are usually organic, are suitable for this purpose, for example starch, sizing material, gelatin, salts of ethercarboxylic acids or ethersulfonic acids of starch or of cellulose, or salts of acidic sulfuric acid esters of cellulose or of starch. Water-soluble polyamides containing acid groups are also suitable for this purpose. Starch derivatives other than those mentioned above may also be used, for example aldehyde starches. Cellulose ethers, such as carboxymethylcellulose (Na salt), methylcellulose, hydroxyalkylcellulose, and mixed ethers, such as methylhydroxyethylcellulose, methylhydroxypropylcellulose, methylcarboxymethylcellulose and mixtures thereof, are preferably used, for example, in amounts of from 0.1 to 5 wt. %, based on the agents.

If desired, the agents may contain a conventional dye transfer inhibitor, preferably in amounts of up to 2 wt. %, in particular 0.1 wt. % to 1 wt. %, which, in a preferred embodiment, is selected from the polymers of vinylpyrrolidone, vinylimidazole, vinylpyridine-N-oxide, or the copolymers thereof. Both polyvinylpyrrolidones having molecular weights of from 15,000 g/mol to 50,000 g/mol and polyvinylpyrrolidones having higher molecular weights of, for example, up to more than 1,000,000 g/mol, in particular from 1,500,000 g/mol to 4,000,000 g/mol, N-vinylimidazole/N-vinylpyrrolidone copolymers, polyvinyloxazolidones, copolymers based on vinyl monomers and carboxylic acid amides, pyrrolidone group-containing polyesters and polyamides, grafted polyamidoamines and polyethyleneimines, polyamine-N-oxide polymers and polyvinyl alcohols can be used. However, it is also possible to use enzymatic systems comprising a peroxidase and hydrogen peroxide or a substance which produces hydrogen peroxide in water. The addition of a mediator compound for the peroxidase, for example an acetosyringone, a phenol derivative or a phenotiazine or phenoxazine, is preferred in this case, it also being possible to additionally use above-mentioned polymeric dye transfer inhibitor active ingredients. Polyvinylpyrrolidone preferably has an average molar mass in the range of from 10,000 g/mol to 60,000 g/mol, in particular in the range of from 25,000 g/mol to 50,000 g/mol. Of the copolymers, those consisting of vinylpyrrolidone and vinylimidazole in a molar ratio of 5:1 to 1:1 with an average molar mass in the range of from 5,000 g/mol to 50,000 g/mol, in particular 10,000 g/mol to 20,000 g/mol, are preferred. In preferred embodiments of the invention, the washing agents are free of additional dye transfer inhibitors of this kind, however.

Washing agents may contain, for example, derivatives of diaminostilbene disulfonic acid or the alkali metal salts thereof as optical brighteners, although they are preferably free of optical brighteners when used as color washing agents. Salts of 4,4'-bis(2-anilino-4-morpholino-1,3,5-triazinyl-6-amino)stilbene-2,2'-disulfonic acid or compounds having a similar structure which, instead of the morpholino group, have a diethanolamino group, a methylamino group, an anilino group or a 2-methoxyethylamino group are suitable, for example. Furthermore, brighteners of the substituted diphenylstyryl type may be present, for example the alkali salts of 4,4'-bis(2-sulfostyryl)diphenyl, 4,4'-bis(4-chloro-3-sulfostyryl)diphenyl, or 4-(4-chlorostyryl)-4'-(2-sulfostyryl)diphenyl. Mixtures of the aforementioned optical brighteners may also be used.

It may be advantageous to add conventional suds suppressors to the agents, in particular when used in mechanical processes. Soaps of natural or synthetic origin having a high proportion of $C_{18}$-$C_{24}$ fatty acids are suitable as suds suppressors, for example. Suitable non-surfactant suds suppressors are, for example, organopolysiloxanes and mixtures thereof with microfine, optionally silanated silicic acid and paraffins, waxes, microcrystalline waxes, and mixtures thereof with silanated silicic acid or bis-fatty acid alkylenediamides. Mixtures of various suds suppressors are also advantageously used, for example those consisting of silicones, paraffins, or waxes. The suds suppressors, in particular silicone- and/or paraffin-containing suds suppressors, are preferably bound to a granular carrier substance that is soluble or dispersible in water. Mixtures of paraffins and bistearylethylenediamide are particularly preferred in this case.

In a preferred embodiment, the agent according to the invention is particulate and contains, in addition to the surfactant of general formula (I), builders, in particular in an amount in the range of from 1 wt. % to 60 wt. %.

In a further preferred embodiment, an agent according to the invention is liquid and contains 1 wt. % to 90 wt. %, in particular 10 wt. % to 85 wt. %, preferably 25 wt. % to 75 wt. %, and particularly preferably 35 wt. % to 65 wt. %, of water, water-miscible solvent, or a mixture of water and water-miscible solvent. Water-miscible solvents include, for example, monohydric alcohols having 1 to 4 C atoms, in particular methanol, ethanol, isopropanol and tert-butanol, diols and triols having 2 to 4 C atoms, in particular ethylene glycol, propylene glycol and glycerol, and mixtures thereof, and the ethers that can be derived from the classes of compounds mentioned. Water-miscible solvents of this kind are present in the agents according to the invention preferably in amounts of no greater than 30 wt. %, in particular from 2 wt. % to 20 wt. %.

In a further preferred embodiment, the agent according to the invention is portioned ready for individual dosing in a chamber made of water-soluble material; the agent contains preferably less than 15 wt. %, in particular in the range of from 1 wt. % to 12 wt. %, of water. A portion is an independent dosing unit having at least one chamber in which product to be dosed is contained. A chamber is a space delimited by walls (e.g. by a film), which space can also exist without the product to be dosed (optionally by changing its shape). A surface coating or a layer of a surface coating is therefore not a wall according to the present invention.

The walls of the chamber are made of a water-soluble material. The water solubility of the material can be determined by means of a square film of said material (film: 22×22 mm with a thickness of 76 μm) fixed in a square frame (edge length on the inside: 20 mm) according to the following measurement protocol. Said framed film is submerged into 800 ml of distilled water, temperature-controlled to 20° C., in a 1-liter beaker with a circular base (Schott, Mainz, beaker 1000 ml, low form), so that the surface of the tensioned film is arranged at a right angle to the base of the beaker, the upper edge of the frame is 1 cm below the water surface, and the lower edge of the frame is oriented in parallel with the bottom of the beaker such that the lower edge of the frame extends along the radius of the base of the beaker and the center of the lower edge of the frame is arranged above the center of the radius of the beaker bottom. The material dissolves within 600 seconds when stirred (stirring speed magnet stirrer 300 rpm, stirring rod: 5 cm long), such that no solid particles at all can be seen with the naked eye.

The walls of the chambers and therefore the water-soluble wrappings of the washing agents according to the invention are preferably formed by a water-soluble film material. Water-soluble packages of this kind can be made either by methods of vertical form-fill sealing or by thermoforming methods.

The thermoforming method generally includes forming a first layer from a water-soluble film material in order to produce bulges for receiving a composition, pouring the composition into the bulges, covering the bulges filled with the composition with a second layer made of a water-soluble film material, and sealing the first and second layers to one another at least around the bulges.

The water-soluble film material is preferably selected from polymers or polymer mixtures. The wrapping may be made up of one or of two or more layers of water-soluble film material. The water-soluble film materials of the first layer and of the additional layers, if present, may be the same or different.

It is preferable for the water-soluble wrapping to contain polyvinyl alcohol or a polyvinyl alcohol copolymer; particularly preferably, it consists of polyvinyl alcohol or polyvinyl alcohol copolymer.

Water-soluble films for producing the water-soluble wrapping are preferably based on a polyvinyl alcohol or a polyvinyl alcohol copolymer of which the molecular weight is in the range of from 10,000 to 1,000,000 gmol$^-$, preferably from 20,000 to 500,000 gmol$^{-1}$, particularly preferably from 30,000 to 100,000 gmol$^{-1}$, and in particular from 40,000 to 80,000 gmol$^{-1}$.

Polyvinyl alcohol is usually prepared by hydrolysis of polyvinyl acetate, since the direct synthesis route is not possible. The same applies to polyvinyl alcohol copolymers, which are prepared accordingly from polyvinyl acetate copolymers. It is preferable for at least one layer of the water-soluble wrapping to include a polyvinyl alcohol of which the degree of hydrolysis is 70 to 100 mol. %, preferably 80 to 90 mol. %, particularly preferably 81 to 89 mol. %, and in particular 82 to 88 mol. %.

Polymers selected from the group comprising acrylic acid-containing polymers, polyacrylamides, oxazoline polymers, polystyrene sulfonates, polyurethanes, polyesters, polyethers, polylactic acid, and/or mixtures of the above polymers may additionally be added to a film material suitable for producing the water-soluble wrapping. It is also possible to copolymerize such monomers on which the polymers are based, individually or in mixtures of two or more, with vinyl acetate.

Polyvinyl alcohol copolymers which include, in addition to vinyl alcohol, an ethylenically unsaturated carboxylic acid, or the salt or ester thereof, are preferred. Polyvinyl alcohol copolymers of this kind particularly preferably contain, in addition to vinyl alcohol, acrylic acid, methacrylic acid, acrylic acid ester, methacrylic acid ester or mixtures thereof; of the esters, $C_{1-4}$ alkyl esters or $C_{1-4}$ hydroxyalkyl esters are preferred. Polyvinyl alcohol copolymers which include, in addition to vinyl alcohol, ethylenically unsaturated dicarboxylic acids as further monomers are also preferred. Suitable dicarboxylic acids are, for example, itaconic acid, maleic acid, fumaric acid, and mixtures thereof, with itaconic acid being particularly preferred.

Suitable water-soluble films for use in the wrappings of the water-soluble packaging according to the invention are films which are sold by MonoSol LLC, for example under the names M8630, C8400 or M8900. Other suitable films include films named Solublon® PT, Solublon® GA, Solublon® KC or Solublon® KL from Aicello Chemical Europe GmbH, or the VF-HP films from Kuraray.

The washing or cleaning agent portion comprising the washing or cleaning agent and the water-soluble wrapping may have one or more chambers. The water-soluble wrappings having a chamber can have a substantially dimensionally stable spherical, rotationally ellipsoidal, cubic, cuboidal or pillow-shaped design with a circular, elliptical, square or rectangular basic shape. The agent may be contained in one or more chambers, if present, of the water-soluble wrapping.

In a preferred embodiment, the water-soluble wrapping has two chambers. In this embodiment, the two chambers may each contain a solid partial composition or a liquid partial composition, or the first chamber contains a liquid partial composition and the second chamber a solid partial composition.

The proportions of the agents contained in the different chambers of a water-soluble wrapping having two or more chambers may have the same composition. Preferably, however, the agents in a water-soluble wrapping having at least two chambers have partial compositions which differ by at least one ingredient and/or by the content of at least one ingredient. Preferably, a partial composition of such agents according to the invention comprises an enzyme and/or a bleach activator and a separate further partial composition comprises peroxidic bleaching agent, the first partial composition thus in particular not comprising peroxidic bleaching agent and the second partial composition in particular not comprising an enzyme or a bleach activator.

Packaging in portions in a water-soluble wrapping allows the user, for an application, to put one or, if desired, more, preferably one, of the portions into the washing machine or dishwasher, in particular into the dispensing chamber of a washing machine, or into a container for carrying out a manual washing or cleaning process. Portion packs of this kind fulfil the consumer's desire for simplified dosing. After the addition of water, the wrapping material dissolves such that the ingredients can be released and take effect in the liquor. Preferably, a portion wrapped in a water-soluble manner weighs 10 g to 35 g, in particular 12 g to 28 g, and particularly preferably 12 g to 15 g, with 0.3 g to 2.5 g, in particular 0.7 g to 1.2 g, of the proportion of the water-soluble wrapping contained in the weight specification being omitted.

The preparation of solid agents according to the invention presents no difficulties and can be carried out in a known manner, for example by spray-drying or granulation, with enzymes and possibly other thermally sensitive ingredients such as, for example, bleaching agents optionally being added separately later. For the preparation of agents having an increased bulk weight, in particular in the range of from 650 g/l to 950 g/l, a method having an extrusion step is preferred.

Liquid or paste-like agents according to the invention in the form of water solutions containing typical solvents are usually prepared by simple mixing of the ingredients, which can be put into an automatic mixer in bulk or as a solution.

EXAMPLES

Example 1: Synthesis of sodium (2-undecyltetrahydrofuro[3,4-d][1,3]dioxol-4-yl) methyl sulfate and sodium 2-undecyltetrahydro-4H-furo[3,2-d][1,3] dioxin-7-yl sulfate A: Preparation of 2-(hydroxymethyl)tetrahydrofuran-3,4-diol 50.0 g (0.329 mol) of ribitol were mixed with 70 ml of 3 molar H2SO4. The reaction mixture was heated under reflux for 24 h. Subsequently, it was cooled in ice water and the sulfuric acid was neutralized by adding 14 g of sodium hydroxide (0.35 mol). The reaction mixture was concentrated under vacuum until a dark-brown syrup formed; this was mixed with 150 ml of ethanol, and the mixture was heated to 60° C. and filtered through a pleated filter. The filtrate was concentrated to 50 vol. % and cooled to −18° C. The precipitate was filtered off and dried under high vacuum. 40.9 g of 2-(hydroxymethyl)tetrahydrofuran-3,4-diol was obtained. Yield: 93%

$^{1}$H-NMR [D$_2$O]: δ=3.54 (dd, J=12.3, 5.1 Hz, 1 H); 3.73 (m, 3 H); 3.98 (m, 2 H); 4.17 (m, 1 H) ppm $^{13}$C-NMR [$_D$2O], δ=61.23; 70.97; 71.50; 72.14; 81.44 ppm B: Preparation of 2-(hydroxymethyl)tetrahydrofuran-3,4-diol and 2-undecyltetrahydro-4H-furo[3,2-d][1,3]dioxin-7-ol:

A solution of 10.00 g of 2-(hydroxymethyl)tetrahydrofuran-3,4-diol (74.6 mmol) in 40 ml of ethanol was mixed with 11 ml of n-dodecanal (49.7 mmol) and 0.2 wt. % of camphor-10-sulfonic acid and stirred at 80° C. for 24 h. After the reaction mixture was cooled to room temperature, it was extracted twice with 25 ml of diethyl ether and 25 ml of dilute aqueous NaCl solution. The combined organic phases were washed with 10 ml of saturated aqueous NaHCO$_3$ solution and dilute aqueous NaCl solution and dried by means of NaSO$_4$. The diethyl ether was removed on a rotary evaporator and the residue dried at 50° C. under high vacuum. 13.65 g of a mixture of 2-(hydroxymethyl)tetrahydrofuran-3,4-diol and 2-undecyltetrahydro-4H-furo[3,2-d][1,3]dioxin-7-ol in the ratio 46:54 was obtained. Yield: 61%.

$^{13}$C-NMR [CDCl$_3$]: δ=14.11; 22.68; 23.92; 23.98; 29.33; 29.50; 29.53; 29.58; 29.61; 29.63; 31.90; 33.40; 33.45; 61.74; 62.01; 62.21; 72.46; 72.72; 80.00; 80.05; 80.97; 81.56; 82.11; 83.92; 84.58; 104.59; 107.60 ppm C: Preparation of Sodium (2-undecyltetrahydrofuro[3,4-d][1,3]dioxol-4-yl) Methyl Sulfate (P1) and Sodium 2-undecyltetrahydro-4H-furo[3,2-d][1,3]dioxin-7-yl sulfate (P2)

A solution of 13.65 g of the mixture obtained in step B of 2-(hydroxymethyl)tetrahydrofuran-3,4-diol and 2-undecyltetrahydro-4H-furo[3,2-d][1,3]dioxin 7-ol (45.43 mmol in 300 ml of acetonitrile was mixed with 8.68 g sulfur trioxide pyridine complex (54.51 mmol, 1.2 eq) and the reaction mixture was stirred at 75° C. for 16 h. Then, 0.5 ml of deionized water was added, and the mixture was stirred for an additional 15 minutes at 75° C. The solvent was removed in the rotary evaporator until a light-brown syrup remained. This syrup was absorbed in 200 ml of ethanol, mixed with 7.25 g of Na$_2$CO$_3$ (68.13 mmol, 1.5 eq) and stirred at 40° C. for 4 days. The mixture was then filtered off by means of silica gel 150 and washed twice with 200 ml of ethanol and with 200 ml of methanol. The filtrate was concentrated in the rotary evaporator and the remaining white/beige solid was dried under high vacuum, washed twice with acetone and removed by centrifugation (7,000 rpm, 10 min). After drying under high vacuum, 7.2 g of P1 and P2 were obtained in a weight ratio of 46:54. Yield: 60%.

$^{13}$C-NMR [D$_2$O]: δ==13.83; 13.86; 22.71; 24.19; 24.43; 29.70; 29.94; 30.05; 30.12; 30.15; 30.24; 32.12; 33.28; 33.55; 67.48; 67.67; 72.68; 73.15; 80.07; 80.98; 81.41; 82.07; 82.11; 82.18; 104.68; 106.72 ppm The critical micelle concentration (CMC) of the mixture of surfactants P1 and P2 was determined by measuring the surface tension of their aqueous solution as a function of concentration at 25° C. and a pH of 8.5 to 0.09 g/l. The interfacial tension of an aqueous solution of the mixture (concentration 1 g/l) with respect to isopropyl myristate at pH 8.5 and 25° C. was measured using the spinning drop method. After 20 minutes, a value of 3 mN/m was produced.

What is claimed is:

1. An anionic surfactant of general formula (I) or of general formula (II) or a mixture thereof,

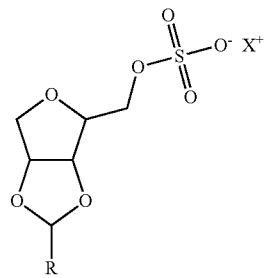

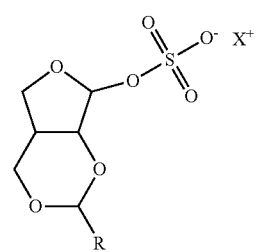

in which R is a linear or branched alkyl, alkenyl, alkylaryl or alkenylaryl group having 5 to 25 C atoms and $X^+$ is a charge-balancing cation.

2. A method for preparing an anionic surfactant of general formula (I) or of general formula (II) or a mixture thereof,

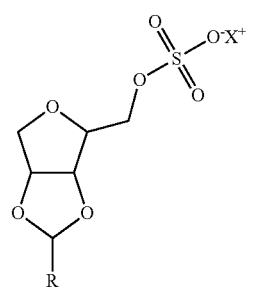

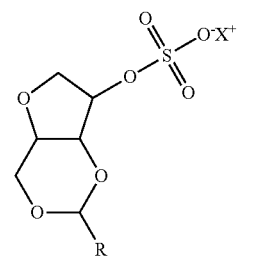

in which R is a linear or branched alkyl, alkenyl, alkylaryl or alkenylaryl group having 5 to 25 C atoms and $X^+$ is a charge-balancing cation, by a) acid-induced separation of water from ribitol, arabitol, xylitol or mixtures thereof, b) reacting the 2-hydroxymethyl-tetrahydrofuran-3,4-diol obtained in this way with an aldehyde RCHO, in which R has the meaning stated above, and c) subsequent sulfation using a sulfating agent and optionally neutralization by subsequent reaction with $X^+OH^-$, $X^+HCO^-_3$ or $X^+_2CO^2_{-3}$, wherein $X^+$ is an alkali metal cation or a grouping $N^+R^1R^2R^3$, in which $R^1$, $R^2$ and $R^3$ are, independently of one another, hydrogen, an alkyl group having 1 to 6 C atoms or a hydroxyalkyl group having 2 to 6 C atoms.

3. A washing or cleaning agent containing an anionic surfactant of general formula (I) or of general formula (II) or a mixture thereof,

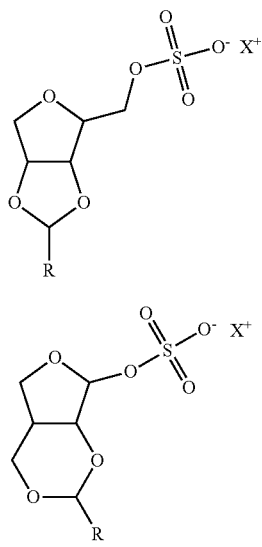

in which R is a linear or branched alkyl, alkenyl, alkylaryl or alkenylaryl group having 5 to 25 C atoms and $X^+$ is a charge-balancing cation.

4. The agent according to claim 3, wherein it contains 1 wt. % to 99 wt. % of the surfactant of general formula (I) or of general formula (II) or a mixture thereof.

5. The agent according to claim 3, wherein it additionally contains up to 99 wt. % of additional surfactant.

6. The agent according to claim 3, wherein it is particulate and contains builders, or in that it is liquid and contains 1 wt. % to 90 wt. % of water, water-miscible solvent or a mixture of water and water-miscible solvent.

7. The agent according to claim 3 wherein it is portioned ready for individual dosing in a chamber made of water-soluble material and contains less than 15 wt. % of water.

8. The surfactant according to claim 1, wherein the compounds of general formula (I) or of general formula (II) or mixtures thereof, R is a linear or branched alkyl group having 7-21 C atoms.

9. The agent according to claim 4, wherein it contains 3 wt. % to 65 wt. % of the surfactant of general formula (I) or of general formula (II) or a mixture thereof.

10. The agent according to claim 5, wherein it additionally contains 3 wt. % to 65 wt. % of additional surfactant.

11. The agent according to claim 6, wherein it contains builders in an amount in the range of from 1 wt. % to 60 wt. %, or in that it is liquid and contains 10 wt. % to 85 wt. % of water, water-miscible solvent or a mixture of water and water-miscible solvent.

12. The agent according to claim 7, wherein the water-soluble chamber contains a range of 1 wt. % to 12 wt. % of water.

13. The method according to claim 2, wherein the compounds of general formula (I) or of general formula (II) or mixtures thereof, R is a linear or branched alkyl group having 7-21 C atoms.

14. The agent according to claim 3, wherein the compounds of general formula (I) or of general formula (II) or mixtures thereof, R is a linear or branched alkyl group having 7-21 C atoms.

* * * * *